(12) United States Patent
Eng (10) Patent No.: US 10,867,704 B2
(45) Date of Patent: Dec. 15, 2020

(54) PHARMACY DATABASE STRUCTURE COMPONENT

(71) Applicant: MediSite Inc., West Bloomfield, MI (US)

(72) Inventor: Edward J. Eng, West Bloomfield, MI (US)

(73) Assignee: MEDISITE INC., West Bloomfield, MI (US)

( * ) Notice: Subject to any disclaimer, the term of this patent is extended or adjusted under 35 U.S.C. 154(b) by 267 days.

(21) Appl. No.: 15/265,044

(22) Filed: Sep. 14, 2016

(65) Prior Publication Data

US 2018/0075211 A1    Mar. 15, 2018

(51) Int. Cl.
| | |
|---|---|
| *G06Q 10/00* | (2012.01) |
| *G16H 50/30* | (2018.01) |
| *G16H 40/20* | (2018.01) |
| *G16H 20/10* | (2018.01) |

(52) U.S. Cl.
CPC ............ *G16H 50/30* (2018.01); *G16H 20/10* (2018.01); *G16H 40/20* (2018.01)

(58) Field of Classification Search
CPC ......... G16H 50/30; G16H 40/20; G16H 20/10
See application file for complete search history.

(56) References Cited

U.S. PATENT DOCUMENTS

| | | | |
|---|---|---|---|
| 8,386,274 B1 | 2/2013 | Pinsonneault | |
| 8,725,532 B1 | 5/2014 | Ringold | |
| 2005/0154627 A1* | 7/2005 | Zuzek | G06Q 30/02 705/2 |
| 2008/0056556 A1* | 3/2008 | Eller | G07G 1/0036 382/142 |
| 2008/0300719 A1* | 12/2008 | Duke | A61J 7/0481 700/244 |
| 2010/0299158 A1* | 11/2010 | Siegel | G06F 19/3456 705/3 |
| 2012/0046970 A1 | 2/2012 | Potts et al. | |
| 2015/0213204 A1* | 7/2015 | Bose | G06F 19/323 705/3 |
| 2016/0004841 A1 | 1/2016 | Power | |
| 2016/0055315 A1* | 2/2016 | Abbott | G06F 19/00 705/2 |

* cited by examiner

*Primary Examiner* — Gabrielle A McCormick
(74) *Attorney, Agent, or Firm* — Brooks Kushman P.C.

(57) ABSTRACT

A data structure embodied on a computer-readable medium having a database schema for accessing and managing pharmacy transactions data in a structured query language (SQL) database. The database schema includes a session data schema representing a relational data table for capturing a plurality of sessions for accessing and managing the SQL database and a pharmacy prescription drug transaction results schema representing parameters for relating prescription drug transaction results with requesters, prescribers and the prescription drug. The session data schema and the pharmacy prescription drug transaction results schema used by a pharmacy business logic application to access and manage the pharmacy drug transaction results in the SQL database.

21 Claims, 4 Drawing Sheets

FULFILLMENT FORM — 400

| Attempt Date | Patient | Drug | MD/Provider | Status | Fulfillment | | History |
|---|---|---|---|---|---|---|---|
| xx-yy-zzzz | Doe, Jane | Drug Name | Provider Name | Open | Filled | Denied | History |
| xx-yy-zzzz | Doe, John | Drug Name | Provider Name | Open | Filled | Denied | History |

402a, 402b, 406, 408, 410

Risk Assessment — 404

| Patient | MD/Provider | Drug |
|---|---|---|
| (!) | (✓) | (✗) |
| (✗) | (!) | (✓) |

View

FIG. 4

CURRENT TRENDS FOR PATIENT AND MD/PROVIDER — 500

| Classification | Patient | MD/Provider |
|---|---|---|
| C2 – C5 | (✗) | (!) |
| C2 | (!) | (✓) |
| C3 | (✗) | (✓) |
| C4 | | (✗) |
| C5 | (✗) | (✓) |

FIG. 5

PHARMACY DATABASE STRUCTURE COMPONENT

TECHNICAL FIELD

Aspects disclosed herein generally relate to a pharmacy database structure component.

BACKGROUND

Pharmacies are frequently faced with the challenge of whether or not to fulfill a request for a prescription drug from a customer. In many instances, the customer may not be authorized to obtain the prescription drug for one or more reasons, such as, the customer has been over-prescribed, the customer's prescription adversely interacts with other prescriptions or medications, and/or the customer does not have a valid prescription for the drug.

SUMMARY

In a first illustrative embodiment, a data structure embodied on a computer-readable medium having a database schema for accessing and managing pharmacy transactions data in a structured query language (SQL) database is disclosed. The database schema includes a session data schema representing a relational data table for capturing a plurality of sessions for accessing and managing the SQL database and a pharmacy prescription drug transaction results schema representing parameters for relating prescription drug transaction results with requesters, prescribers and the prescription drug. The session data schema and the pharmacy prescription drug transaction results schema used by a pharmacy business logic application to access and manage the pharmacy drug transaction results in the SQL database.

In a second illustrative embodiment, a computer system is disclosed. The computer system includes a means for generating a pharmacy database structure component for previous requests for a prescription drug by a requestor that are stored in at least two different retail pharmacy transaction computer systems, a means for populating the information relating to the previous requests for the prescription drug into the pharmacy database structure component, and a means for configuring for display the pharmacy database structure component such that a determination of whether to fulfill the request for the prescription drug is made by a pharmacist.

In a third illustrative embodiment, a computer system for determining whether a pharmacist should fulfill a prescription drug request by a requester is disclosed. The computer system includes first retail pharmacy transaction computer system including a first database having a first format and a first data structure. The computer system also includes a second retail pharmacy transaction computer system including a second database having a second format and a second data structure. The first retail pharmacy transaction computer system may be, for example, of one of the following types: an independent pharmacy system, a regional pharmacy chain or a large, or national chain. The second retail pharmacy transaction computer system may of a same type or a different type as the first retail pharmacy transaction computer system, but the second system is a system independent and not communicative with the first system, in at least one embodiment. The first or second retail pharmacy transaction computer system or different computer system includes a computer having non-transitory memory for storing machine instructions that are to be executed by the computer. The machine instructions when executed by the computer cause the computer to: receive a request for a prescription drug that includes requester identifying information, transmit a request to the first and second retail pharmacy transaction computer systems for information relating to any previous requests for the prescription drug by the requester based on the prescription drug and the requester identifying information, receiving from the first and second retail pharmacy transaction computer systems the information relating to any previous requests for the prescription drug by the requester, including any completed or denied requests for the prescription drug, the date of any such completed or denied requests, and the location of each completed or denied request), generate a pharmacy database structure component for previous requests for the prescription drugs logically categorizing the previous requests, populate the information relating to any previous requests for the prescription drug into the pharmacy database structure component, and configure for display the pharmacy database structure component such that a determination of whether to fulfill the request for the prescription drug is made by a pharmacist.

In a fourth illustrative embodiment, a non-transitory computer-readable medium having computer-readable instructions stored thereon that are executed by a processor is disclosed. The computer-readable instructions are configured to be executed to direct the processor to: receive a request for a prescription drug that includes requester identifying information, transmit a request to the first and second retail pharmacy transaction computer systems for information relating to any previous requests for the prescription drug by the requester based on the prescription drug and the requester identifying information, receive from the first and second retail pharmacy transaction computer systems the information relating to any previous requests for the prescription drug by the requester, including any completed or denied requests for the prescription drug, the date of any such completed or denied requests, and the location of each completed or denied request), generate a pharmacy database structure component for previous requests for the prescription drugs logically categorizing the previous requests, populate the information relating to any previous requests for the prescription drug into the pharmacy database structure component, and configure for display the pharmacy database structure component such that a determination of whether to fulfill the request for the prescription drug is made by a pharmacist.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Pharmacies are frequently faced with the challenge of whether or not to fulfill a request for a prescription drug from a customer. In many instances, the customer may not be authorized to obtain the prescription drug for one or more reasons, such as, the customer has been over-prescribed, the customer's prescription adversely interacts with other prescriptions or medications, and/or the customer does not have a valid prescription for the drug. Pharmacists often rely upon their previous interactions with the customer to make a decision regarding a prescription drug request. This is not an option for customers that are new to a pharmacy. Pharmacists do not have adequate computerized systems to aid the pharmacist in decided whether or not to fulfill a prescription drug request from customers that are new to a pharmacy or have been to other pharmacies. These issues may be especially acute with respect to controlled substances and controlled medications, such as, C2-C5 schedule prescription drugs.

The existing computer prescription drug transaction systems do not adequately provide the necessary and appropriate prescription drug transaction information across different pharmacy computer system platforms. Disparate and disassociated pharmacy retailers do not share prescription drug transaction data about prescription drug requests in a real-time and useful manner.

The following proposed computer systems and computerized methods have failed to provide adequate technical solutions.

U.S. Pat. Publ. No. 2016/0055315, to Abbott, discloses an inappropriate prescription, prescriber or prescribing location identification system and method. The Abbott system and method do not provide prescription drug transaction data in a usable format for a pharmacist to decide whether or not to fulfill a prescription drug request.

The I-STOP/PMP—Internet System Tracking Over-Prescribing-Prescription Monitoring Program Article discloses a Prescription Monitoring Program (PMP) Registry. The PMP Registry provides practitioners with direct, secure access to view dispensed controlled substance prescription histories for their patients. This registry is a specific service for doctors and other health practitioners with authorization to issue prescription and controlled prescription drugs. The registry does not provide a system in which prescription drug transaction information may be accessed and monitored across several different disparate and disassociated pharmacy prescription drug transaction systems.

U.S. Pat. No. 8,386,274, to Pinsonneault, discloses systems and methods for a prescription safety network utilizing eligibility verification transactions. The systems and methods require a patient to enroll in the prescription safety network program for utilizing a prescribed drug or product. Enrollment may not detect that the patient is not authorized to receive prescriptions for prescription drugs and products. The methods and systems provide an isolated and closed approach that does not factor in the challenges of an open system of disassociated pharmacy computer systems.

U.S. Pat. Publ. No. 2012/0046970, to Potts, discloses a controlled substance system that may include a controlling entity having a database. The system relies upon associating data with a unique identifier, and is focused on the distribution and dispensing of medical marijuana. The system does not operate in and is not capable of addressing an environment of different pharmacy computer system platforms and database structures. Potts computerized service requires a finite universe of customers to carry out an "active" token for self-identification before fulfillment can take place. The Potts service cannot be successfully applied to an environment of different pharmacy system platforms to present risk factors associated with fulfilling a prescription drug request.

U.S. Pat. No. 8,725,532, to Ringold, discloses computer systems and methods for monitoring controlled substance distribution. The systems and methods include receiving a healthcare transaction at a service provider computer. Counters associated with total scripts prescribed by a healthcare provider and a class of controlled substances may be incremented upward in view of a healthcare transaction being approved by a claims processor. Ringold does not operate in an environment of pharmacy computer systems. Ringold also does not accommodate prescription drug transaction data from multiple, disparate pharmacy computer systems and/or platforms.

U.S. Pat. Publ. No. 2016/0004841, to Power, discloses a computer system and method that focuses on known customers, via a unique numbering system and nationwide database, and known customers' controlled prescription drug purchase and consumption. The Powers system and method do not relate information between multiple, disparate pharmacy computer systems and/or platforms to provide risk correlations based on approved or denied previous prescription drug purchases from all of the multiple, disparate pharmacy computer systems and/or platforms.

On the other hand, the pharmacy computer system, the computer-readable medium, and the database structure component aspects disclosed herein provide a non-abstract, technological improvement over the known proposals. These technological improvements are rooted in a pharmacy database structure component that is populated with information from at least two different retail pharmacy systems that do not communicate with each other. The information relates to previous requests for a prescription drug and the result of those previous requests. The information is logically categorized such that it may be structured into a multi-dimensional risk assessment matrix for customer, prescriber and prescription drug.

The pharmacy computer system, the computer-readable medium, and the pharmacy database structure component aspects disclosed herein include a particular arrangement of generic and conventional computer components to provide a method and system for determining whether a pharmacist should fulfill a prescription drug request by a customer within the specific environment of a pharmacy. In one or more examples, the present invention provides a non-conventional and non-generic arrangement of computer components. The structure of the pharmacy database component is not disclosed or suggested by the prior art as disclosed herein. For example, the pharmacy database structure component includes relational pharmacy transaction data from at least two different retail pharmacy transaction computer systems.

In one or more examples, the methods and systems set forth herein provide significantly more than a generic way to determine whether or not to fulfill a request for a prescription drug, such as, a controlled prescription drug, based on a pharmacy database structure component. The pharmacy database structure component can be used to generate a multi-dimensional risk assessment matrix for prescription requesters, prescribers and prescription drugs.

The pharmacy database structure component is inextricably tied to a machine for implementing a pharmacy fulfillment request determination service among many retail pharmacy transaction computer systems, which do not otherwise communicate with each other because of competitive and privacy concerns. The exemplar aspects do more than a nominal recitation of a computer.

Aspects herein relate to tangible devices, e.g., a pharmacy computer system, a pharmacy computer readable medium, and a pharmacy database structure component. The devices operate in the environment of controlled prescription drugs, which would be consumed by customers, if a controlled prescription drug request is fulfilled. The tangible devices and controlled prescription drugs work in combination to provide a specific manner of providing computer tools and structures for determining whether or not to fulfill a controlled prescription drug request.

Figure 1:
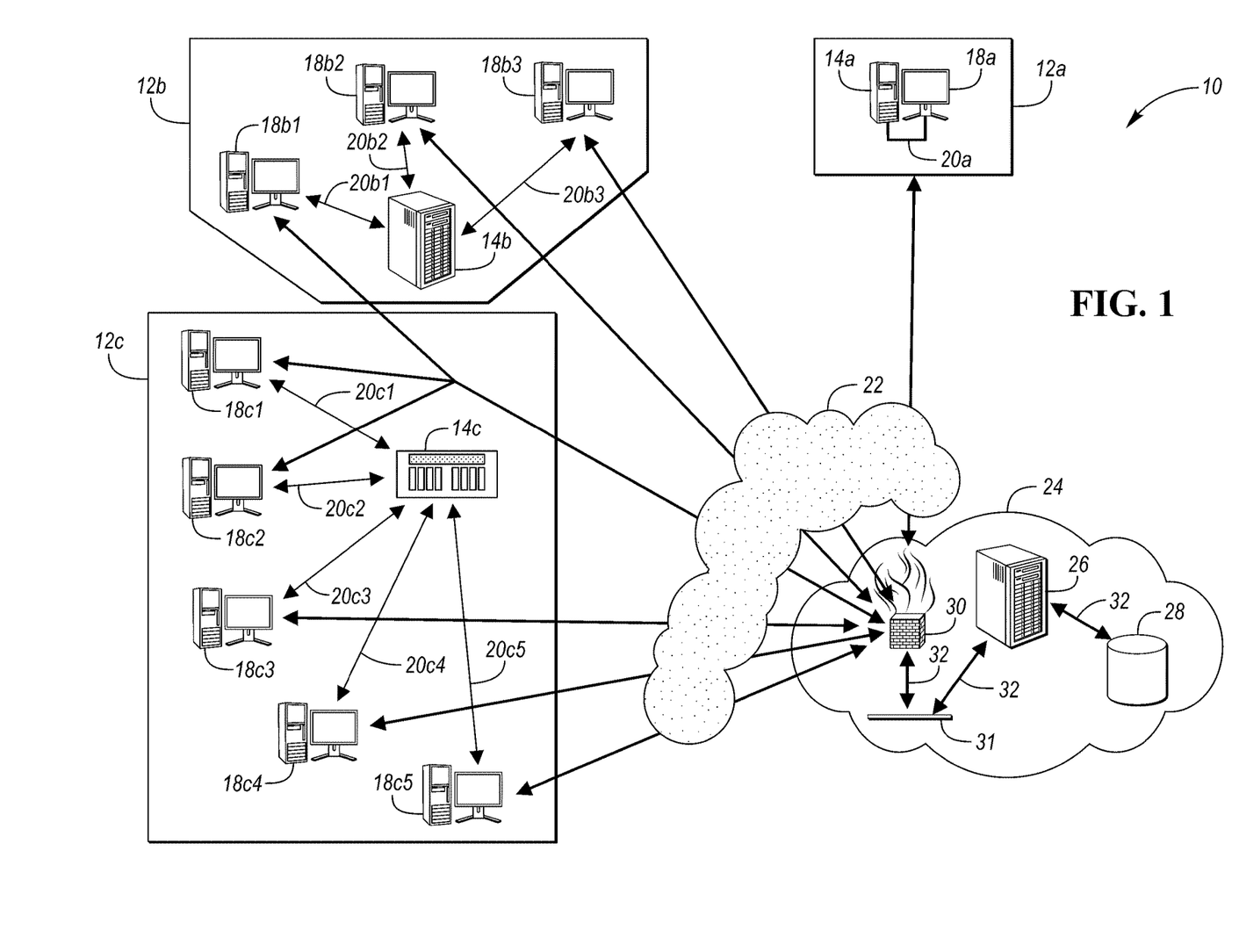
FIG. 1 illustrates an example network computer system architecture for providing an environment for a prescription drug transaction access and monitoring computer system, computer-readable medium, and a pharmacy database structure component.

Example aspects operate in a distributed computing environment having a number of pharmacy transaction computer systems. FIG. 1 depicts an example network computer system architecture including an example distributed computing environment of retail pharmacy transaction computer systems. Distributed computing environment 10 includes retail pharmacy transaction computer systems 12a, 12b and 12c. For example, retail pharmacy transaction system 12a can be an independent pharmacy system with one or a small number of locations, retail pharmacy transaction system 12b can be a computer system of a regional pharmacy chain, such as, Publix® or Kroger® supermarket chain, which also has a pharmacy at each location, and retail pharmacy transaction system 12c can be a computer system of a large, national chain, such as Rite Aid®, Walgreens® or CVS® pharmacy chain. Retail pharmacy transaction systems 12a, 12b and 12c include servers 14a, 14b and 14c, respectively (which each include a database), and user computers 18a, 18b1-3 and 18c1-5, respectively. User computers 18a, 18b1-3 and 18c1-5 are configured to access servers 14a, 14b and 14c, respectively, over internal communication networks 20a, 20b1-3 and 20c1-5, respectively. Servers 14a, 14b and 14c and user computers 18a, 18b1-3 and 18c1-5, respectively, are configured to transmit and receive data from the other over internal communication networks 20a, 20b1-3 and 20c1-5, respectively. Each of the retail pharmacy transaction systems 12a, 12b and 12c are configured to transmit and receive data over external network 22. Each of the user computers 18a, 18b1-3 and 18c1-5, are configured to display pharmacy information through a user interface. This user interface may be executed locally on each of the user computers 18a, 18b1-3 and 18c1-5, and/or remotely by each of the servers 14a, 14b and 14c.

Figure 2:
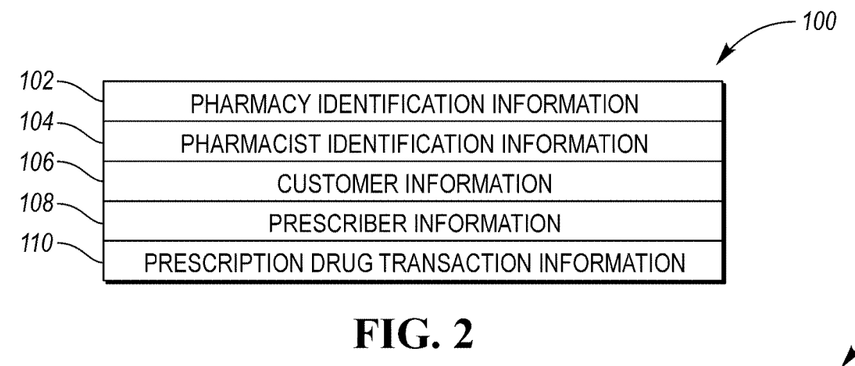
FIG. 2 illustrates an example database system for prescription drug transaction data relating to current sessions or transactions in progress.

Non-limiting examples of general classes of pharmacy transaction information 100 housed in databases include pharmacy identification information 102, pharmacist identification information 104, customer information 106, prescriber information 108, and prescription drug information 110, as shown in FIG. 2. While these general classes of pharmacy information 100 may be housed in each of the databases, they are stored in different formats and data structures. Accordingly, the pharmacy transaction information 100 of all databases is not interoperable to make real-time prescription fulfillment decisions and is non-usable by unrelated pharmacies.

The pharmacy identification information 102 may include, without limitation, a transaction number, a merchant code, a pharmacy location number, a location category code, longitude of location, latitude of location, address of location, zip code of location, carrier code of the location and/or hot spot score for the location.

The pharmacist identification information 104 may include, without limitation, a pharmacist's first name, a pharmacist's last name, a pharmacist's national license number, a pharmacy employee number, a logon date, a logon time in, and a logon time out. The log date and time relate to when the pharmacist logs on and logs off of the retail pharmacy transaction computer systems 12a, 12b and 12c.

The customer information 106 may include, without limitation, a customer's first name, a customer's middle name, a customer's last name, a customer's date of birth, a customer's driver's license number, a customer's address, a customer's social security number, a franchise/merchant code for the customer, and/or franchise/merchant customer number for the customer.

The prescriber information 108 may include, without limitation, a prescriber's first name, a prescriber's last name, a prescriber's Drug Enforcement Agency (DEA) license number, a prescriber's National Provider Identifier (NPI) license number, and/or a prescriber's clinic/office address.

The prescription drug information 110 may include brand name, generic name, preference of brand name or generic name, order dosage, order quantity, refill number and refill cycles in days.

Referring back to FIG. 1, a prescription drug transaction access and monitoring computer system 24 is depicted. As depicted in FIG. 1, computer system 24 is contained within a cloud computing environment. Computer system 24 includes a server 26, database 28, firewall 30, switch 31 and computer software residing on the server 26. Firewall 30 ensures that computer system 24 is Health Insurance Portability and Accountability Act (HIPAA) compliant. Data transmitted from and received by computer system 24 pass through firewall 30 using a key service, such as, SSL POS version 1.2, to encrypt the data. Switch 31 permits load balancing of incoming network connections from external network 22. Server 26 can be placed in multiple locations for load balancing and fail over network redundancy. Server 26 is configured to access database 28 over internal communication network 32. Server 26 and firewall 30 are configured to transmit and receive data from the other over internal communication network 32. Computer system 24 is configured to transmit and receive data over external network 22 from retail pharmacy transaction computer systems 12a, 12b and 12c. This configuration permits server 26 to collect, query and report controlled prescription drug transaction data from retail pharmacy transaction computer systems 12a, 12b and 12c. However, pharmacy transaction computer systems 12a, 12b and 12c are not configured and cannot communicate with each other to share data relating to prescription drug transactions. Client computers 18a, 18b1-3 and 18c1-5 are each configured to provide a secure access point to the computer software residing on server 26 such that each is configured to display pharmacy transaction information through a user interface and receive information input by the user, typically a pharmacist. Accordingly, the software residing on server 26 can be accessed as Software as a Service ("SaaS"). This user interface may be executed locally on each of the user computers 18*a*, 18*b*1-3 and 18*c*1-5 and/or remotely by the server 26.

The server 26 may include various types of computing apparatus, such as a computer workstation, a server, a desktop computer, a virtual server instance executed by a cluster or group of dedicated servers or computers, or some other computing system and/or device. Computing devices, such as the server 26, generally include a memory on which computer-executable instructions may be maintained, where the instructions may be executable by one or more processors of the computing device. Such instructions and other data may be stored using a variety of computer-readable media. A computer-readable medium (also referred to as a processor-readable medium or storage) includes any non-transitory (e.g., tangible) medium that participates in providing data (e.g., instructions) that may be read by a computer (e.g., by the processor of the server 26). In general, processors receive instructions, e.g., from the memory via the computer-readable storage medium, etc., and executes these instructions, thereby performing one or more processes, including one or more of the processes described herein. Computer-executable instructions may be compiled or interpreted from computer programs created using a variety of programming languages and/or technologies, including, without limitation, and either alone or in combination, Java, C, C++, C#, Fortran, Pascal, Visual Basic, Java Script, Perl, PL/SQL, etc. In one embodiment, the computer-executable instructions are compiled or interpreted from computer programs created in C#, .Net, Service Stack, SQL, PHP (for Linux) and/or ASP .Net (for Windows) and Rest API." In one embodiment, server 26 runs Windows Enterprise 12 and a full version of IIS with ADO .net and ASP.net and WCF (SaaS) for HIPAA compliance purposes.

The database 28 may be one such application included on the storage of the server 26. The database 28 may include instructions that, when loaded into memory and executed by the server 26 cause the database 28 to perform database functionality including the storage, update, and retrieval of relational information. Databases or data repositories such as the database 28 may include various kinds of mechanisms for storing, accessing, and retrieving various kinds of data, including a hierarchical database, a set of files in a file system, an application database in a proprietary format, a relational database management system (RDBMS), etc. In one embodiment, database 28 is a relational database in Microsoft SQL Server. The database 28 may employ features of the computer operating system of the server 26, and may be accessed via the internal communication network 32 in a variety of manners. The databases 28 may also utilize the file system via the computer operating system, and may store and retrieve files stored in various formats. An RDBMS generally employs the Structured Query Language (SQL) in addition to a language for creating, storing, editing, and executing stored procedures. More specifically, the database 28 may be configured to maintain pharmacy transaction information in a novel pharmacy database structure component. In one embodiment, the novel pharmacy database structure component is double encrypted. The component is stored in an encrypted state within database 28, which is housed on an encrypted hard drive.

The internal communication network 32 may be configured to facilitate secure communication between internal components of the computer system 24. Accordingly, the internal communication network 32 may provide communication services between the server 26 and database 28. As one aspect of providing security for the communications, the internal communication network 32 may limit or exclude communications from devices other than retail pharmacy transaction computer systems 12*a*, 12*b* and 12*c*. The database 28 may be configured to maintain information such that it may be accessible only by authorized parties. Additionally or alternately, the internal communication network 32 is configured to support encryption of communications between the internal devices. The server 26 may include an application programming interface (API) accessible via the user computer to users of the computer system 24. The API may be configured to provide access to the data stored in the database 28 based on a user account or application requesting access.

As described above, the data classes shown in FIG. 2 for each retail pharmacy transaction computer system 12*a*, 12*b* and 12*c* are isolated from one another. Accordingly, the data structures storing the pharmacy data structures for each retail pharmacy transaction computer system 12*a*, 12*b* and 12*c* do not relate the pharmacy data from each computer systems 12*a*, 12*b* and 12*c*. Unlike the isolated and disparate data structures of computer systems 12*a*, 12*b* and 12*c*, the prescription drug transaction access and monitoring computer system 24 includes a pharmacy database structure that is unified and provides for source-neutral pharmacy data collection and pharmacy data relationships between customers, prescribers and prescription drugs.

Figure 3:
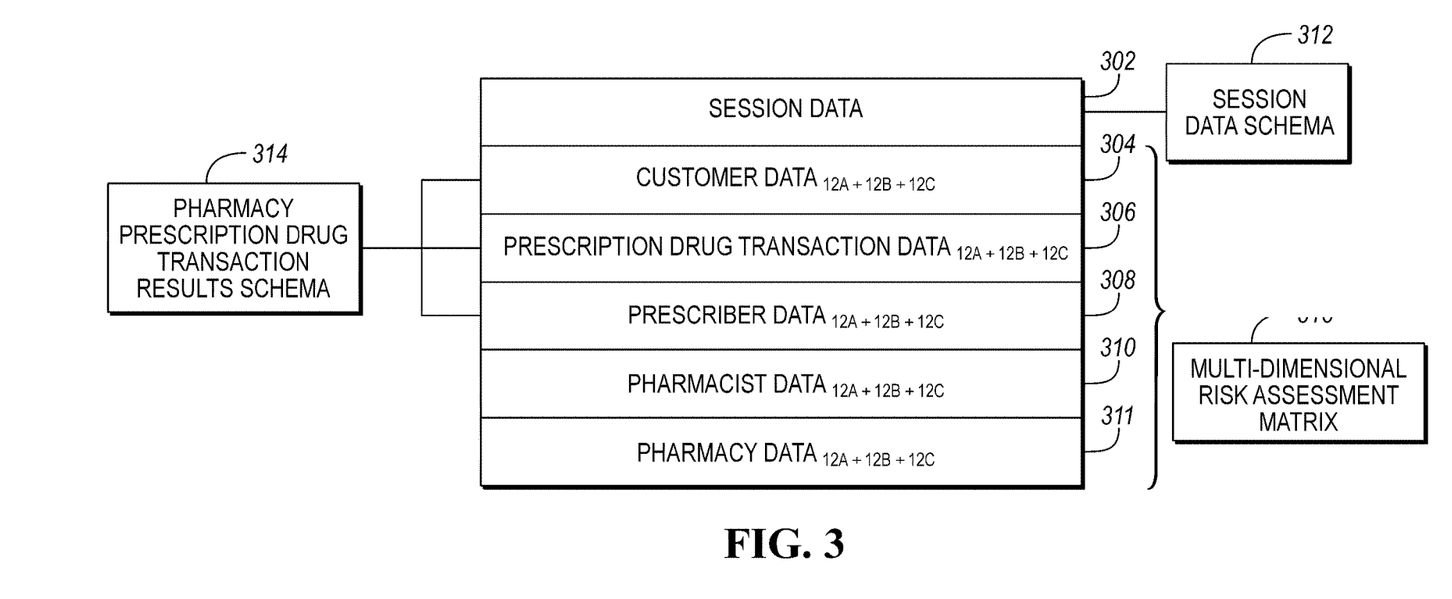
FIG. 3 illustrates an example pharmacy database structure component for prescription drug transaction information.

FIG. 3 shows an example of a pharmacy database structure component 300. The prescription drug transaction access and monitoring computer system 24 in connection with the pharmacy database structure component 300 transforms isolated pharmacy transaction data of the multiple and disparate pharmacy transaction systems 12*a*, 12*b* and 12*c* into the pharmacy database structure component 300, which is an electronic tool for a pharmacist to make an informed decision regarding whether or not to prescribe a controlled prescription drug to an individual requesting the controlled prescription drug. The pharmacy database structure component 300 is a particular form of a database component. The structure of the pharmacy database component 300 does not exist in any singular pharmacy transaction system 12*a*, 12*b* and 12*c*, yet the pharmacy database component 300 is structured in such a manner that it can unify the pharmacy data from the disparate pharmacy transaction systems 12*a*, 12*b* and 12*c*. In this way, the pharmacy database component 300 is neutral to all of the pharmacy transaction systems 12*a*, 12*b* and 12*c*. In addition, the computer system 24 is configured to cloak, or otherwise encode or encrypt, sensitive and confidential pharmacy information transmitted from the pharmacy transaction systems 12*a*, 12*b* and 12*c*, including any information that would allow a user of the present system to associate the data with a specific pharmacy merchant, location or chain. This cloaking capability is used to preserve the confidentiality of one pharmacy's information from a competitive pharmacy's viewing.

The computer system 24 obtains the pharmacy database information from each pharmacy transaction system 12*a*, 12*b* and 12*c* as its input. The computer system 24 uses the input pharmacy information to populate the pharmacy database component 300. The pharmacy database component 300 includes at least five (5) different interrelated data buckets, e.g., session data 302, customer data 304, prescription drug transaction data 306, prescriber data 308, pharmacist user data 310, and pharmacy data 311.

The session data 302 may include, without limitation, user identification login for computer system 24, log on password for computer system 24, log on date, log on time in, and log on time out. The session data 302 may also include data relating to each controlled prescription drug requested during a session and data associated with whether the request was filled or denied.

The customer data 304 may include, without limitation, first name, middle initial, last name, date of birth, drivers' license number, address, social security, franchise/merchant code, and franchise/merchant customer number.

The prescription drug transaction results data 306 may include, without limitation, brand name, generic name, preferred name, order dosage, order quantity, refill number, refill cycle in days. This data is stored for each prescription drug requested during a session of server 26. For instance, the prescription drug could be a controlled drug or substance, such as, a C2-C5 drug. For each of these prescription drugs requested, the associated prescription drug transaction results are stored in pharmacy database structure component 300. Data 306 may also include filled confirmation information and denied confirmation information. The filled confirmation information includes the identity of the prescription drug requested and filled, a confirmation of the fulfillment, and the reason(s) the prescription drug was filled. The denied confirmation information includes the identity of the prescription drug requested and denied, a confirmation of the denial, and the reason(s) the prescription drug request was denied.

The prescriber data 308 may include, without limitation, first name, last name, DEA license number, NPI license number, and clinic/office address.

The pharmacist user data 310 may include, without limitation, user first name, user last name, user pharmacist national license number, and pharmacy employee number.

The pharmacy data 311 may include a transaction number, a merchant code, a pharmacy location number, a location category code, longitude of location, latitude of location, address of location, zip code of location, carrier code of the location and/or hot spot score for the location. The hot spot score is a range of scores indicative of the likelihood that the location is a hot spot for abuse of prescription drug requests.

The pharmacy database component 300 includes a session data schema 312. The session data schema 312 includes a relational data table for capturing a plurality of sessions. The relational data table relates the session data to the other data within the pharmacy database component 300, which is received from at least two different and disparate retail pharmacy transaction computer systems 12a, 12b and 12c. The session data schema 312 allows for access and management of the data in the pharmacy database component 300, which can be an SQL database.

The pharmacy database component 300 also includes a pharmacy prescription drug transaction results schema 314. Schema 314 includes parameters to relate prescription drug transaction results from at least two different and disparate retail pharmacy transaction computer systems 12a, 12b and 12c, with customers, prescribers and the prescription drug relating to a transaction. The schema 314 applies to each and every prescription drug stored in the pharmacy database component 300.

The session data schema 312 and the pharmacy prescription drug transaction results schema 314 can be used by a pharmacy business logic application, such as software residing on a computer-readable medium of server 26, to access and manage the pharmacy drug transaction results in the pharmacy database component 300.

The pharmacy prescription drug transactions results schema 314 is configured to logically categorize previous prescription drug requests and dispositions from at least two different and disparate retail pharmacy transaction computer systems 12a, 12b and 12c. The logical categorization can be based on a chronological order based on the dates of previous requests and/or dispositions.

The pharmacy database structure component 300 may also include a multi-dimensional risk assessment matrix. The risk assessment matrix assesses the risk associated with prescribing the requester the requested prescription drug, e.g., the requester is not authorized to obtain the controlled prescription drug, the requester has been over-prescribed, or the customer's prescription adversely interacts with other prescriptions or medications. The pharmacy database structure component 300 may be transmitted to a government agency server computer, such as a law enforcement agency, or an insurance company server computer for further analysis.

The risk assessment is automatically performed by server 26 by reference to the aggregated prescription drug transaction, prescriber and requester information in the pharmacy database structure component 300. In one example applied to C2-C5 schedule controlled substances and drugs, the pharmacy database structure component 300 is queried for data relating to the patient/customer/requester, the pharmacy location, and/or the prescriber.

Regarding the patient/customer/requestor, the component 300 can be queried for one or more of the following (per unit time, where applicable): (i) number of purchase attempts for specific C2-C5 prescription drugs, (ii) number of purchase attempts for any C2-C5 prescription drug in the same schedule; (iii) number of purchase attempts for any and all C2-C5 prescription drugs; (iv) number of denials of specific C2-C5 prescription drug requested; (v) number of denials for any C2-C5 prescription drug in the same schedule; (vi) number of denials for specific C2-C5 prescription drug requested; (vii) number of purchases of any C2-C5 prescription drug outside of home zip code by a certain number of miles, e.g., 10, 20 or 30 miles; (viii) number of purchases of any C2-C5 prescription drug outside of an area dominant influence (ADI) by a certain number of miles, e.g., 10, 20 or 30 miles; (ix) number of purchases of any C2-C5 prescription drug within a hot spot zone; (x) number of prescribers currently writing C2-C5 prescription drugs for a patient; and/or (xi) number of prescribers for the specific C2-C5 prescription drug for the patient.

Regarding the pharmacy location, the component 300 can be queried for one or more of the following: (i) pharmacy location is a hot spot; (ii) the requested C2-C5 prescription drug is on a warning list, e.g., a warning list provided by administrator for the pharmacy; and/or (iii) pharmacy user associated with more than benchmark C2-C5 prescription drug sales.

Regarding the prescriber, the component 300 can be queried for one or more of the following: (i) prescriber office location within hot spot zone; (ii) prescriber authored more than a threshold level (e.g., 20, 30 or 40) of the same C2-C5 drug being requested; (iii) prescriber authored greater than a threshold value (e.g., 40, 50 or 60) of any C2-C5 prescription drug; (iv) any prescriber patient denied same C2-C5 prescription drug being requested; (v) any prescriber patient denied any C2-C5 prescription drug; (vi) any prescriber patient purchased any C2-C5 prescription drug more than a certain number of miles, e.g., 10, 20 or 30 miles outside of ADI; and/or (vii) prescriber on "watch list" per local authorities.

The values of these queries relating to the patient/customer/requester, the pharmacy location, and/or the prescriber are categorized to obtain a level of risk associated with fulfilling the prescription request. In one example, the levels of risk can be associated with color indicators, such as green, yellow and red. The green indicator may indicate the current data stored in the component 300 is not currently considered a controlled prescription drug sales risk for the requested prescription drug. The yellow indicator may indicate that the current data stored in the component 300 suggest more interaction with the requester may be appropriate before deciding whether or not to fulfill the prescription request. The red indicator may indicate that the current data stored in the component 300 that fulfilling the prescription request is not recommended due to previously recorded information about the customer's controlled prescription drug transaction history, including request denials and controlled prescription consumption history.

Figures 4, 5:
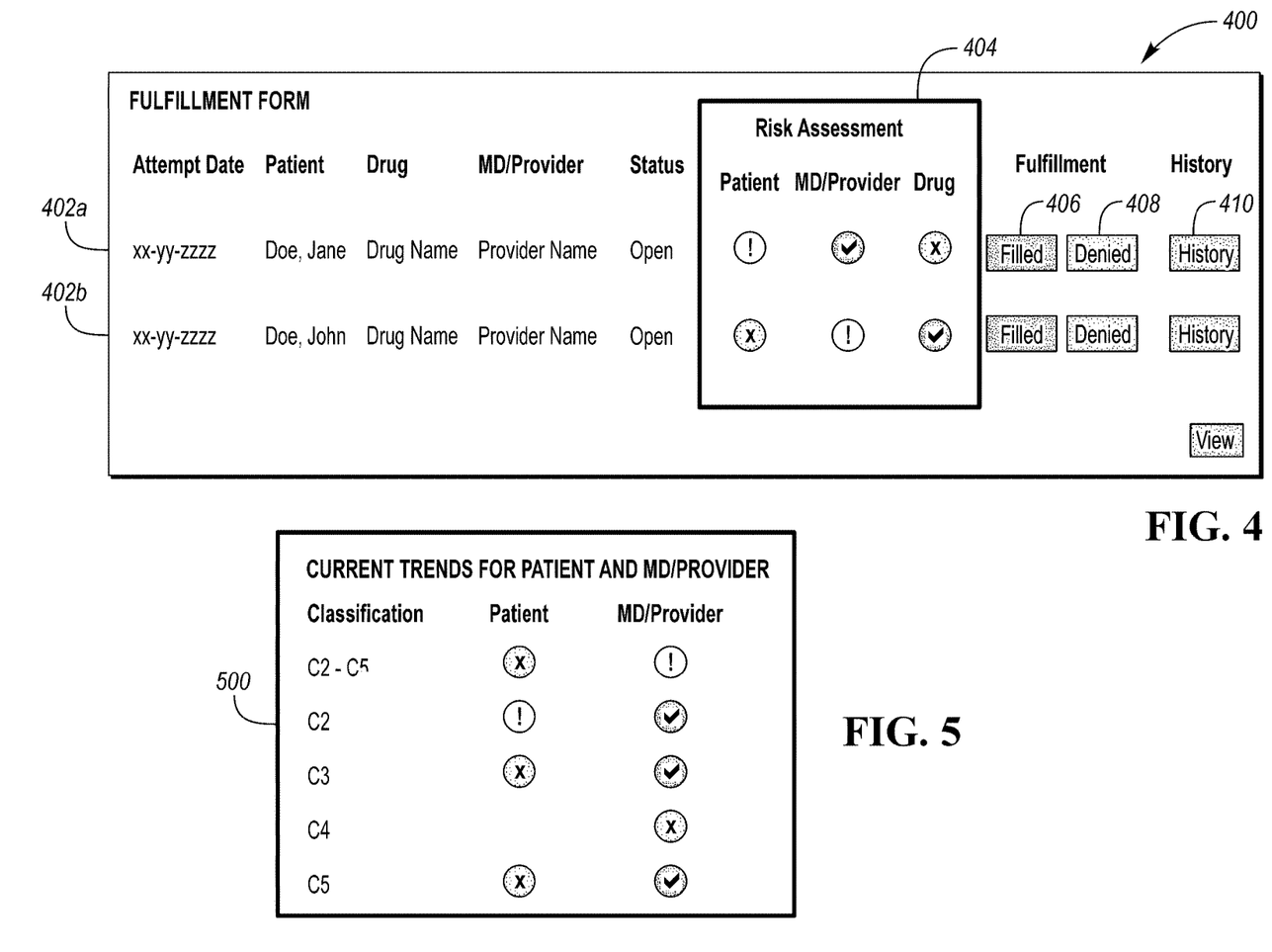
FIG. 4 illustrates an example user interface for outputting data indicative of a multi-dimensional risk assessment matrix for a customer, a prescriber and a prescription drug.
FIG. 5 illustrates an example user interface for outputting data indicative of an aggregated history of the multi-dimensional risk assessment matrix for the customer, the prescriber and the prescription drug.

FIG. 4 illustrates an example user interface 400 for outputting a multi-dimensional risk assessment for customer, prescriber and controlled prescription drugs. The user interface 400 includes the controlled prescription drugs currently in consideration for fulfillment at 402a and 402b. For each fulfillment request attempt 402a and 402b, the user interface 400 displays attempt date, patient name, prescription drug, provider, attempt status, and data indicative of the multi-dimensional risk assessment matrix 404, click buttons 406 and 408 for fulfilling or denying the controlled prescription drug request, and click button 410 for displaying patient purchase or denial history for the specific controlled prescription drug. As shown in FIG. 4, a different icon can be displayed for different risk levels, e.g., green, yellow and red icons for green, yellow and red risk level indicators.

FIG. 5 illustrates an example user interface 500 for outputting an aggregated history of the multi-dimensional risk assessment for requester, prescriber and prescription drugs. As shown in FIG. 5, data indicative of the multi-dimensional risk assessment matrix can be displayed for the patient and prescriber for a number of different controlled prescription drugs. The ability to provide and display this information is a result of the schemas 312 and 314 and matrix 316 of the pharmacy data component structure 300.

Figure 6:
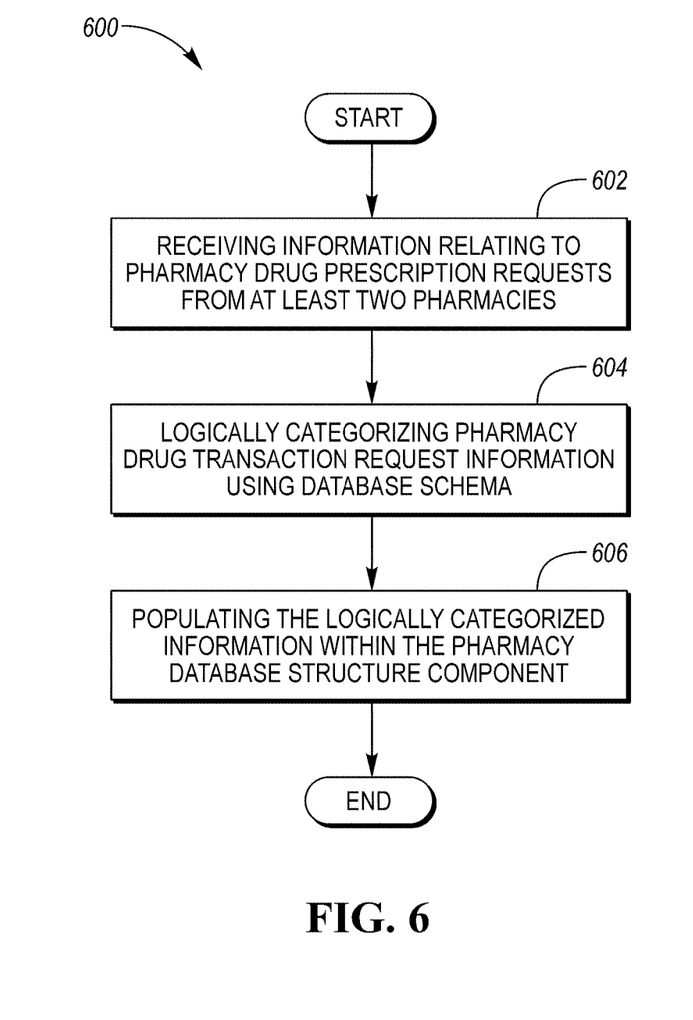
FIG. 6 illustrates an example process for generating a pharmacy database structure component.

FIG. 6 illustrates an example process 600 for generating a pharmacy database structure component. The process 600 may be performed, for example, by software residing on a computer-readable medium of the server 26 or user computers 18a, 18b1-3 and 18c1-5 configured to provide a secure access point to the computer software residing on server 26.

At operation 602, the computer software receives information relating to pharmacy drug prescription requests from at least two pharmacies. The information may include information relating to any previous requests for a prescription drug made by a requester, including completed or denied requests for the prescription drug, the date of any such completed or denied requests, and the location of each completed or denied request.

At operation 604, the computer software logically categorizes pharmacy drug transaction request information using a database schema, for example, pharmacy prescription drug transactions results schema 314. The pharmacy prescription drug transactions results schema 314 is configured to logically categorize previous prescription drug requests and dispositions from at least two different and disparate retail pharmacy transaction computer systems 12a, 12b and 12c. The logical categorization can be based on a chronological order based on the dates of previous requests and/or dispositions.

At operation 606, the computer software populates the logically categorized information within the pharmacy database structure component 300. The information is populated into data buckets 304, 306, 308, 310 and 311 as shown in FIG. 3.

Figure 7:
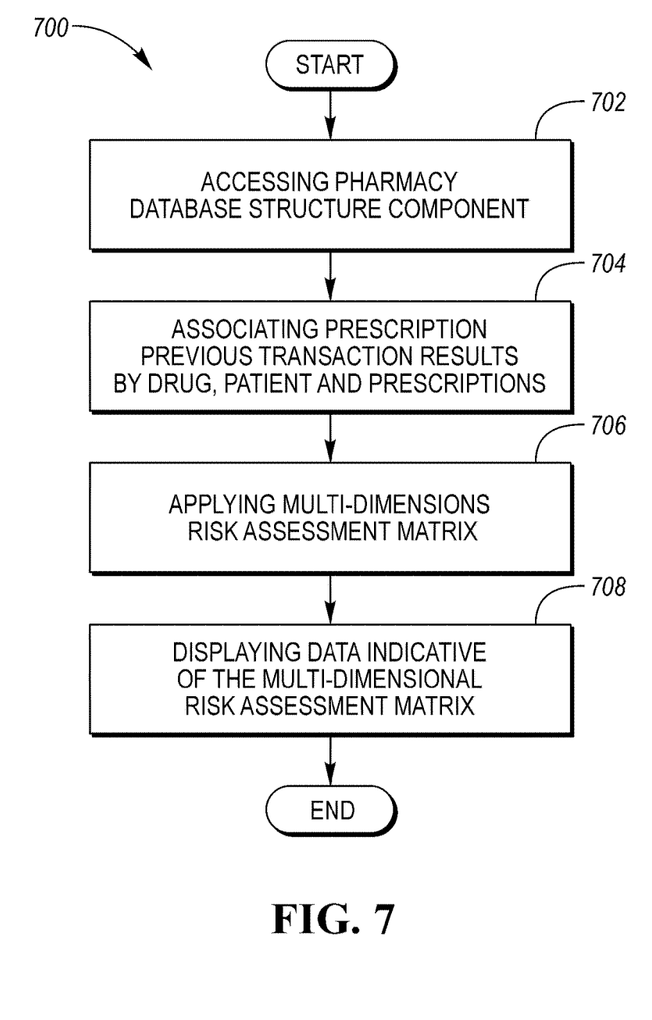
FIG. 7 illustrates an example process for providing the pharmacy database structure component in the context of deciding whether or not to fulfill a prescription drug request.

FIG. 7 illustrates an example process for providing the pharmacy database structure component in the context of deciding whether or not to fulfill a prescription drug request. The process 700 may be performed, for example, by software residing on a computer-readable medium of the server 26 or user computers 18a, 18b1-3 and 18c1-5 configured to provide a secure access point to the computer software residing on server 26.

At operation 702, the computer software accesses the pharmacy database structure component 300. Once accessed, the pharmacy database structure component 300 associates prescription drug transaction results by drug, patient and prescriber (operation 704). At operation 704, the pharmacy database structure component 300 applies the multi-dimensional risk assessment matrix. The results of this application can be used to display data indicative of the multi-dimensional risk assessment matrix on a user interface generated by the computer software.

With regard to the processes, systems, methods, heuristics, etc., described herein, it should be understood that, although the steps of such processes, etc., have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention. For example, the pharmacy database structure component 300 may be used for senior medication mitigation management. Individuals, e.g., senior citizens of ages 65+, may have multiple ailments or conditions that are treated with multiple medications and/or controlled prescription drugs. The pharmacy database structure component 300 can be used for pharmacies and their professional staff to help mitigate over-medication and/or conflicting medication used by senior adults.

What is claimed is:

1. A computer system comprising:
   a means for generating a pharmacy database structure component for previous completed requests and previous denied requests for a drug prescribed by a prescriber and requested by a requestor that are stored in at least two different retail pharmacy transaction computer systems including a first retail pharmacy transaction computer system and a second retail pharmacy transaction computer system, the first retail pharmacy transaction computer system including a first database of prescription drug transactions, the second retail pharmacy transaction computer system including a second database of prescription drug transactions, and the first and second retail pharmacy transaction computer systems are not configured to communicate with each other to share data relating to prescription drug transactions;

a means for populating information relating to the previous completed requests and previous denied requests for the drug into the pharmacy database structure component;

a means for generating a multi-dimensional risk assessment matrix for the requestor, the prescriber and the prescription drug by reference to the previous completed requests and the previous denied requests populated into the pharmacy database structure component; and a means for configuring for display a user interface including the multi-dimensional risk assessment matrix to share data relating to the prescription drug transactions of the first database with the second retail pharmacy transaction computer system and to share data relating to the prescription drug transactions of the second database with the first retail pharmacy transaction computer system, a fulfillment click button and a denial click button, the fulfillment click button is configured to be selected by a pharmacist to fulfill the fulfillment request, and the denial click button is configured to be selected by the pharmacist to deny a fulfillment request for the drug to mitigate over-medication and/or conflicting medication in connection with the fulfillment request.

2. The computer system of claim 1, further comprising a means for transmitting the pharmacy database structure component and the multi-dimensional risk assessment matrix to a government agency server computer and/or an insurance company server computer for an analysis by the government agency server computer and/or the insurance company server computer in connection with the fulfillment request.

3. A computer system for determining whether a pharmacist should fulfill or deny a fulfillment request by a requester for a drug prescribed by a prescriber, the computer system comprising:
   a first retail pharmacy transaction computer system including a first database of prescription drug transactions and having a first format and a first data structure;
   a second retail pharmacy transaction computer system including a second database of prescription drug transactions and having a second format and a second data structure, the first format and/or first data structure of the first database are different than the second format and/or second data structure of the second database, the first and second retail pharmacy transaction computer systems are not configured to communicate with each other to share data relating to the prescription drug transactions of the first and second databases,
   a server computer having non-transitory memory for storing machine instructions that are to be executed by the server computer, the machine instructions when executed by the server computer causes the server computer to:
      receive the fulfillment request for the drug prescribed by the prescriber, the fulfillment request includes requester identifying information;
      transmit a request to the first and second retail pharmacy transaction computer systems for information relating to previous completed requests and previous denied requests for the drug by the requester based on the drug and the requester identifying information;
      receive from the first and second retail pharmacy transaction computer systems the information relating to the previous completed requests and previous denied requests for the drug, including a date of such previous completed requests and previous denied requests and a location of each previous completed request and previous denied request;
      generate a pharmacy database structure component for previous completed requests and previous denied requests received from the first and second retail pharmacy transaction computer systems for the drug logically categorizing the previous completed requests and previous denied requests;
      populate the information relating to the previous completed requests and previous denied requests for the drug into the pharmacy database structure component;
      generate a multi-dimensional risk assessment matrix for the requestor, the prescriber and the prescription drug by reference to the previous completed requests and the previous denied requests populated into the pharmacy database structure component; and
      configure for display a user interface including the multi-dimensional risk assessment matrix to share data relating to the prescription drug transactions of the first database with the second retail pharmacy transaction computer system and to share data relating to the prescription drug transactions of the second database with the first retail pharmacy transaction computer system, a fulfillment click button and a denial click button, the fulfillment click button is configured to be selected by the pharmacist to fulfill the fulfillment request, and the denial click button is configured to be selected by the pharmacist to deny the fulfillment request to mitigate over-medication and/or conflicting medication in connection with the fulfillment request.

4. The computer system of claim 3, wherein the pharmacy database structure component includes the multi-dimensional risk assessment matrix.

5. The computer system of claim 3, wherein the machine instructions when executed by the server computer causes the server computer to generate the pharmacy database structure component for the previous completed requests and previous denied requests for the drug logically categorizing the previous completed requests and previous denied requests in a chronological order based on the dates of the previous completed requests and previous denied requests.

6. The computer system of claim 3, wherein the machine instructions when executed by the server computer causes the server computer to:
   repeat the transmit configuration to obtain updated information relating to the previous completed requests and previous denied requests; and
   automatically generate an updated pharmacy database component based on the updated information relating to the previous completed requests and previous denied requests.

7. The computer system of claim 6, wherein the repeat and automatically generate configurations are capable of being executed independent of the first receive configuration.

8. The computer system of claim 3, wherein the machine instructions when executed by the server computer causes the server computer to:
  determine whether the requester identifying information is true or false based on the pharmacy database structure component.

9. The computer system of claim 3, wherein the requester identifying information includes a requester ID number.

10. The computer system of claim 3, wherein the machine instructions operate whether or not the requester is registered in the first or second retail pharmacy transaction computer system.

11. The computer system of claim 3, wherein the machine instructions when executed by the computer causes the computer to:
  transmit the pharmacy database structure component and the multi-dimensional risk assessment matrix to a government agency server computer and/or insurance company server computer for an analysis by the government agency server computer and/or the insurance company server computer for an analysis by the government agency server computer and/or the insurance company server computer in connection with the fulfillment request.

12. The computer system of claim 3, wherein the prescription drug is a C2-C5 prescription drug.

13. The computer system of claim 3, wherein the information relating to the previous completed requests and previous denied requests for the prescription drug includes a plurality of relationships between the requester and a plurality of prescribers.

14. The computer system of claim 3, wherein the machine instructions when executed by the server computer causes the server computer to:
  transmit the pharmacy database structure component to a third pharmacy computer system.

15. The computer system of claim 3, wherein the machine instructions when executed by the computer causes the computer to cloak the location of each previous completed request and previous denied request to maintain the confidentiality of the location of each previous completed request and previous denied request of a first retail pharmacy associated with the first retail pharmacy transaction computer system and a second retain pharmacy associated with the second pharmacy transaction computer system.

16. The computer system of claim 3, wherein the multi-dimensional risk assessment matrix includes different risk levels and a different risk icon for each different risk level.

17. A non-transitory computer-readable medium having computer-readable instructions stored thereon that are configured to be executed by a processor to:
  receive a fulfillment request for a drug prescribed by a prescriber that includes requester identifying information;
  transmit a request to first and second retail pharmacy transaction computer systems for information relating to previous completed requests and previous denied requests for the drug by the requester based on the drug and the requester identifying information, the first retail pharmacy transaction computer system including a first database of prescription drug transactions, the second retail pharmacy transaction computer system including a second database of prescription drug transactions, and the first and second retail pharmacy transaction computer systems are not configured to communicate with each other to share data relating to prescription drug transactions;
  receive from the first and second retail pharmacy transaction computer systems the information relating to the previous completed requests and previous denied requests for the drug by the requester, including previous completed requests and previous denied requests for the drug, a date of each previous completed request and previous denied request, and a location of each previous completed request and previous denied request;
  generate a pharmacy database structure component for the previous completed requests and previous denied requests received from the first and second retail pharmacy transaction computer systems for the drug logically categorizing the previous completed requests and previous denied requests;
  populate the information relating to the previous completed requests and previous denied requests for the drug into the pharmacy database structure component;
  generate a multi-dimensional risk assessment matrix for the requestor, the prescriber and the prescription drug by reference to the previous completed requests and the previous denied requests populated into the pharmacy database structure component; and
  configure for display a user interface including the multi-dimensional risk assessment matrix to share data relating to the prescription drug transactions of the first database with the second retail pharmacy transaction computer system and to share data relating to the prescription drug transactions of the second database with the first retail pharmacy transaction computer system, a fulfillment click button and a denial click button, the fulfillment click button is configured to be selected by a pharmacist to fulfill the fulfillment request, and the denial click button is configured to be selected by the pharmacist to deny the fulfillment request to mitigate over-medication and/or conflicting medication in connection with the fulfillment request.

18. The non-transitory computer-readable medium of claim 17, wherein the computer-readable instructions are further configured to be executed by a processor to generate the pharmacy database structure component for the previous completed requests and previous denied requests for the drug logically categorizing the previous completed requests and previous denied requests in a chronological order based on the dates of the previous completed requests and previous denied requests.

19. The non-transitory computer-readable medium of claim 17, wherein the pharmacy database structure component includes the multi-dimensional risk assessment matrix.

20. The non-transitory computer-readable medium of claim 17, wherein the computer-readable instructions are further configured to be executed by a processor to:
  repeat the transmit configuration to obtain updated information relating to the previous completed requests and previous denied requests; and
  automatically generate an updated pharmacy database component based on the updated information relating to the previous completed requests and previous denied requests.

21. The non-transitory computer-readable medium of claim 17, wherein the computer-readable instructions are further configured to be executed by a processor to transmit the pharmacy database structure component and the multi-dimensional risk assessment matrix to a government agency server computer and/or an insurance company server computer for an analysis by the government agency server computer and/or the insurance company server computer in connection with the fulfillment request.

\* \* \* \* \*